United States Patent [19]

Tubin

[11] 4,118,946

[45] Oct. 10, 1978

[54] PERSONNEL COOLER

[76] Inventor: Eddie Sam Tubin, 4419 Fulton, Sherman Oaks, Calif. 91403

[21] Appl. No.: 744,318

[22] Filed: Nov. 23, 1976

[51] Int. Cl.² ............................................. F25B 19/00
[52] U.S. Cl. ..................... 62/514 R; 62/384;
62/515; 126/204; 128/379; 128/403; 150/2.2; 165/46
[58] Field of Search ............ 62/515, 529, 530, 514 R, 62/384; 126/204, 400; 165/46; 128/402, 403, 379, 380; 150/2.2, 2.3, 2.4, 2.6

[56] References Cited

U.S. PATENT DOCUMENTS

| | | | |
|---|---|---|---|
| 2,438,643 | 3/1948 | Moore | 62/530 |
| 3,233,662 | 2/1966 | Yuen | 128/403 |
| 3,242,979 | 3/1966 | Shlosinger | 165/46 |
| 3,868,945 | 3/1975 | Konopka et al. | 126/271 |

Primary Examiner—Ronald C. Capossela
Attorney, Agent, or Firm—Wills, Green & Mueth

[57] ABSTRACT

A flexible sheet or garment to be worn on or around the human body, or body member for cooling and having two flexible plastic sheets or films which are joined or adhered to form two tortuous, adjacent, generally coextensive, non-communicating fluid paths, one of said fluid paths being substantially and permanently filled with a viscous liquid heat transfer media and the other of said fluid paths being in communication with a reservoir of pressurized gas, means between said reservoir and other fluid path for regulating the flow of pressurized gas through said other fluid path and a pressure relief means in said other fluid path and positioned at a point remote from said reservoir to limit the gas pressure and gas flow rate in said other fluid path; and means for holding said sheet or garment in place on or around the human body, or body member.

7 Claims, 8 Drawing Figures

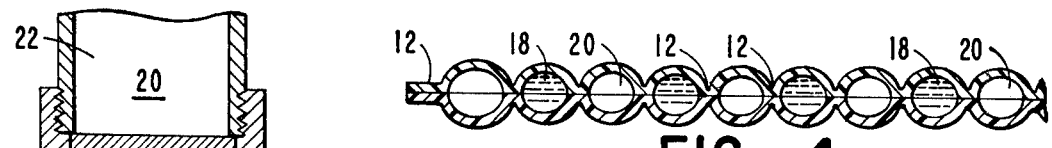
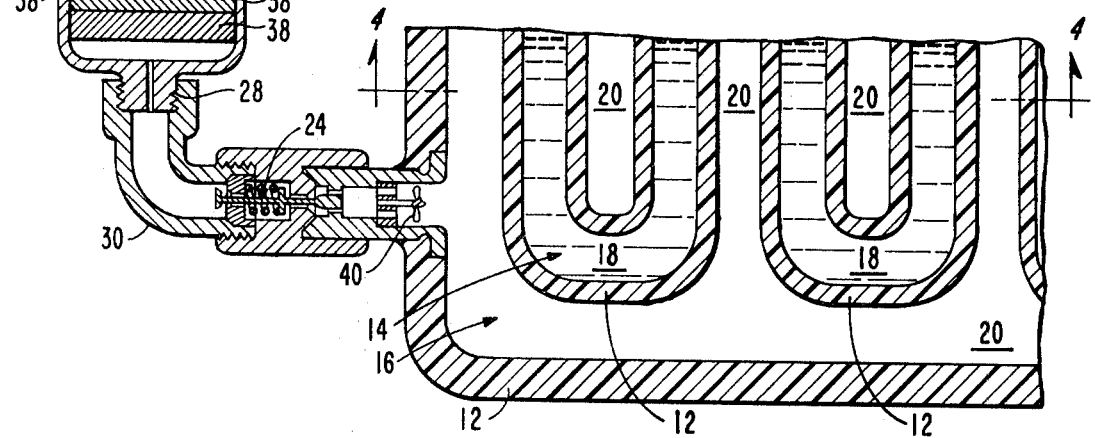
FIG.-4
FIG.-3
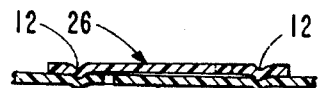
FIG.-5
FIG.-6
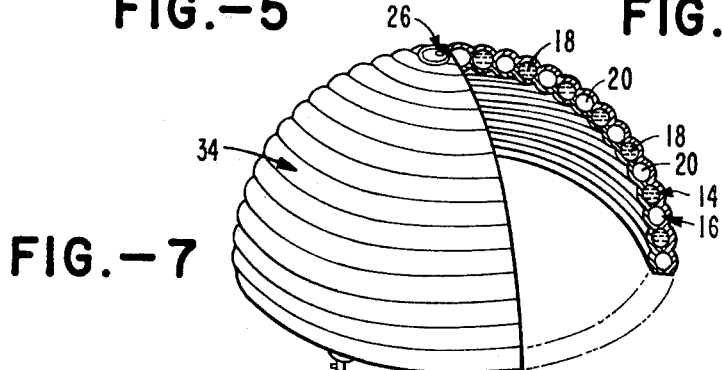
FIG.-7
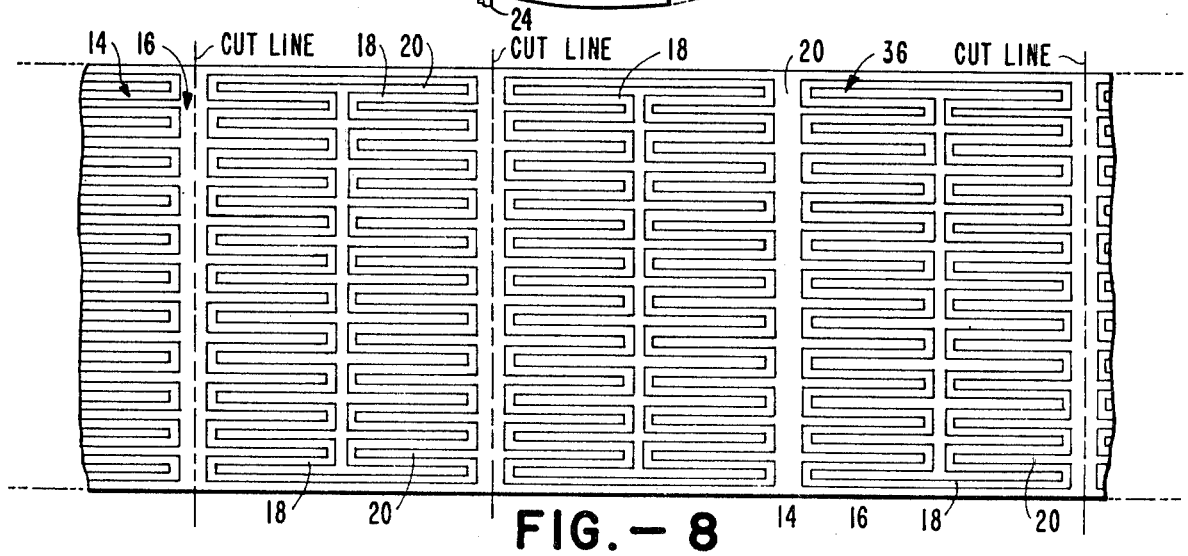
FIG.-8

PERSONNEL COOLER

BACKGROUND OF THE INVENTION

It is a problem to protect workmen, farmers, and the like who must work in open exposed areas in hot climates from the effects of heat and sunlight. Such persons are subject to suffering heat prostration unless great care is taken to avoid prolonged exposure. A significant amount of time and productivity is lost due to necessity for rest stops and complete work stoppages during the late morning and afternoon hours in tropical and desert climates. Analogous problems are also encountered by various military forces throughout the world. The present invention is intended to solve these persistent problems in a surprising simple and inexpensive manner, and it is to be expected that my invention will be rapidly adopted, particularly in the tropical and desert areas of the world.

SUMMARY OF THE INVENTION

Briefly, this invention comprises a flexible sheet or garment to be worn on or around the human body, or body member for cooling and having two flexible plastic sheets or films which are joined or adhered to form two tortuous, adjacent, generally co-extensive, non-communicating fluid paths, one of said fluid paths being substantially and permanently filled with a viscous liquid heat transfer media, and the other of said fluid paths being in communication with a reservoir of pressurized gas, means between said reservoir and other fluid path for regulating the flow of pressurized gas through said other fluid path and a pressure relief means in said other fluid path and positioned at a point remote from said reservoir to limit the gas pressure and gas flow rate in said other fluid path; and means for holding said sheet or garment in place on or around the human body, or body member.

It is an object of this invention to provide a novel means for cooling the body of persons exposed to intense heat and/or humidity.

More particularly, it is an object of this invention to provide a novel cooling garment for the human body.

It is a further object of this invention to provide a cooling garment which can be easily recharged with cooling gas, and otherwise is free of field service requirements.

These and other objects and advantages of my invention will be available from the detailed description which follows.

It should be noted that, while not found by any theory, it is believed that the heat transfer efficiency of the device of my invention is due to the fact that the permanent viscous fluid in the open fluid path has an excellent heat pick up from the human body, and that the more or less continuous flow of pressurized gas in the other fluid path, being generally and tortuously adjacent to the first fluid path, efficiently transfers heat from the viscous liquid to the gas which gas and its heat is continuously discharged to the exterior.

DESCRIPTION OF THE PREFERRED EMBODIMENTS

Turning to the drawings:

FIG. 3 is a sectional view of the lower left hand corner of the device of FIG. 2.

FIG. 4 is a section taken along the line 4—4 in FIG. 3.

FIG. 5 is a sectional view of the pressure relief valve in the "closed" position.

FIG. 6 is a sectional view of the pressure relief valve of FIG. 5 in the "open" position.

FIG. 7 is a perspective view, partially broken away to show the cross-sectional configuration, of another embodiment of my invention, this embodiment being a cap to be worn on the head.

FIG. 8 is a plan view of a sheet of material embodying this invention and adapted to be cut up, formed or joined if desired into any type or size garment, and to be worn on the body or body member.

Figure 1:
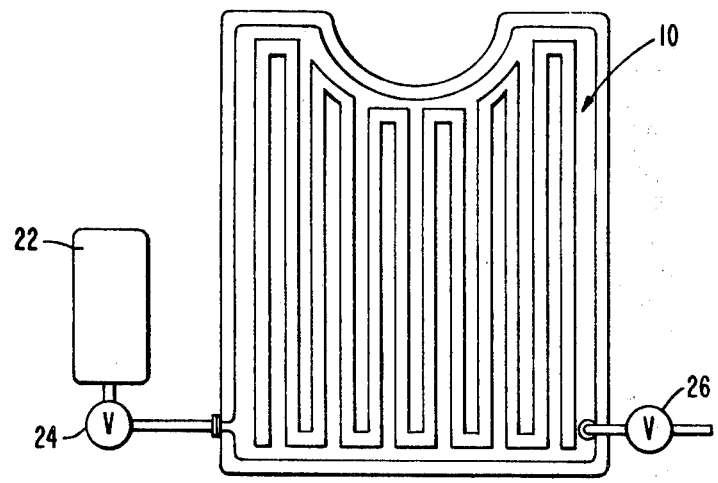
FIG. 1 is a front schematic view of one embodiment of this invention, in this case, a vest to be worn on the upper torso.
Figure 2:
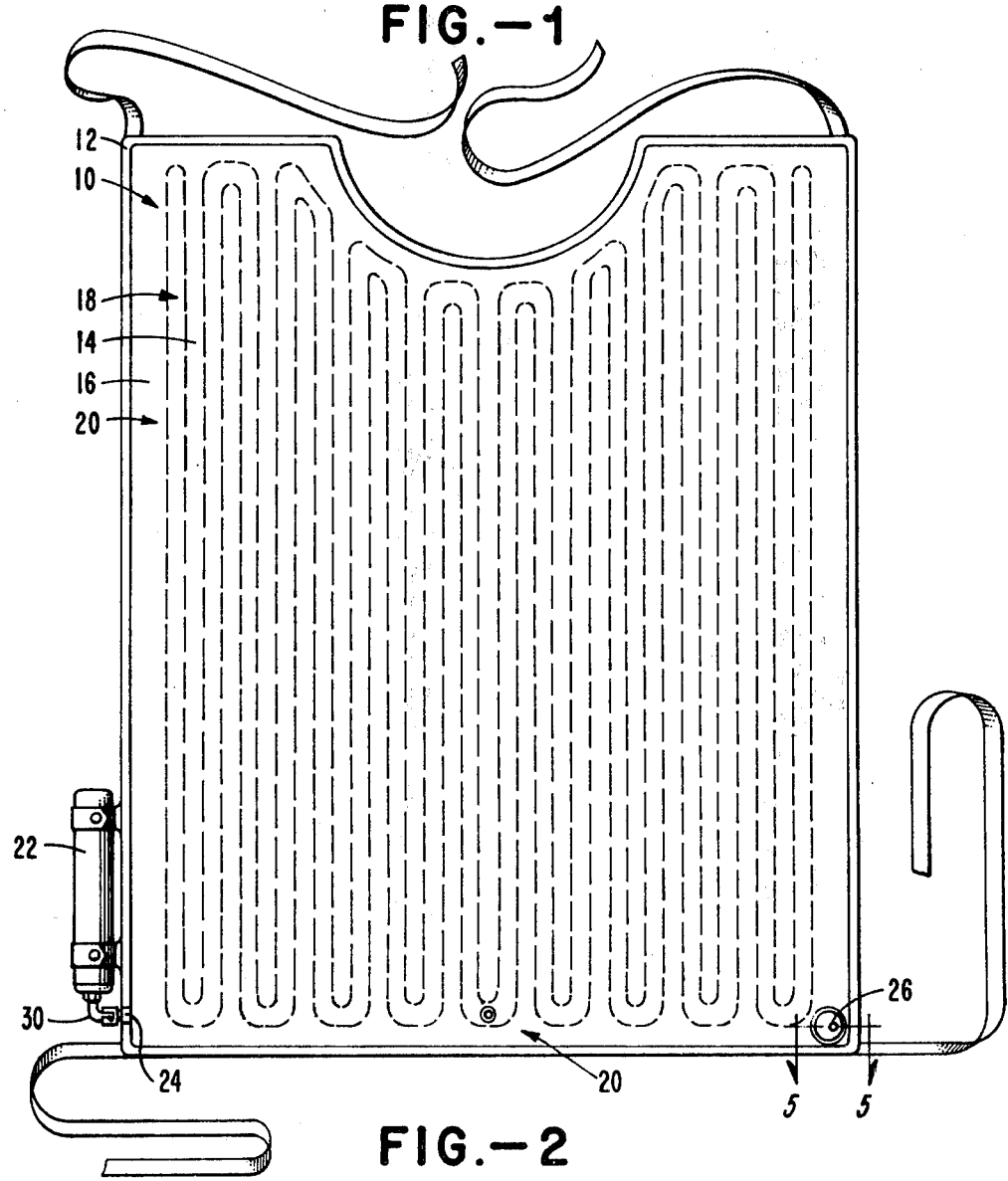
FIG. 2 is a front view of an actual embodiment of such a vest.

The vest 10 of FIGS. 1 and 2 is formed of two superposed sheets of flexible, flaccid plastic film such as vinyl or polyethylene which are joined by heat seal areas 12 as shown in FIG. 3. The joindure could also be accomplished using adhesive, etc. In any case, the areas of joindure form two tortuous fluid paths 14 and 16. These fluid paths are non-communicating with each other, but are generally adjacent which facilitates the transfer of heat from the one path to the other.

The fluid path 14 is permanently filled with a viscous liquid 18, perferably one having a high specific heat of over 1.0 which can act as a heat sink. The fluid path 16 is for pressurized gas 20 such as $CO_2$ continuously supplied by a reservoir 22. The flow of the pressurized gas 20 into fluid path 16 is controlled by feed valve 24. The pressure level within fluid path 16 is regulated by pressure relief valve 26 which is pre-set to avoid over-pressurization or ballooning of the garment. Pressure relief valve 26 is preferably positioned at a point at or near that end of fluid path 16 which is opposite or remote from feed valve 24. The gas released by relief valve 26 vents to the atmosphere and is the site of ultimate heat dissipation.

The reservoir 22 is provided with a threaded coupling 28 to the line 30 leading to feed valve 24 to permit the ready exchange or replacement of reservoirs of pressurized gas.

One preferred embodiment of pressure relief valve is the flap valve arrangement 32 shown in the open and closed positions.

As will be evident to those skilled in the art from the within discussion and drawings, this invention is adapted to any type of garment or wrap for the body such as the cap 34 shown in FIG. 7. Similarly, the invention is applicable to a coat, arm, leg or torso wrap, head band, and in specialized applications, for the legs and/or feet.

It is also to be understood that the sheet material of this invention can be made in the form of a continuous strip ala a bolt of cloth from which a desired configuration can be cut and the edges heat sealed or otherwise closed to form the two adjacent but non-communicating fluid paths. Such a sheet 36 is illustrated in FIG. 8.

Optionally, the gas flow rate can be further controlled by the selection and type of porous ceramic or carborundum discs 38 positioned at the opening of reservoir 22. The movement of the gas 20 can also be facilitated by a rotating wheel 40 which creates turbulence in the gas and prevents the formation of a local spot of gas concentration.

It is also to be understood that the outer surface of the device which lies along the skin of the wearer can be provided with a fabric layer. Also, said outer surface can be provided with flocking.

Having fully described the invention it is intended that it be limited only by the scope of the appended claims.

I claim:

1. A flexible panel to be worn adjacent a portion of the human body for cooling, which comprises:

two flexible plastic sheets which are joined to form two tortuous, adjacent, generally co-extensive, non-communicating fluid paths, one of said fluid paths being substantially and permanently filled with a viscous liquid heat transfer media and the other of said fluid paths being in communication with a reservoir of pressurized gas;

means between said reservoir and said other fluid path for regulating the flow of pressurized gas through said other fluid path and a pressure relief means in said other fluid path and positioned at a point remote from said reservoir to limit the gas pressure and gas flow rate in said other fluid path; and means for holding said sheet in place adjacent a portion of the human body.

2. The structure of claim 1 in the form of a continuous sheet.

3. The structure of claim 1 in the form of a garment.

4. The structure of claim 3 in the form of a vest.

5. The structure of claim 3 in the form of a head cover.

6. The structure of claim 3 in the form of a coat.

7. The structure of claim 1 wherein the sheets are heat sealed.

* * * * *